United States Patent
Al-Qasem

(10) Patent No.: US 8,863,595 B2
(45) Date of Patent: Oct. 21, 2014

(54) SAMPLE EXTRACTION DEVICE

(75) Inventor: Sadeq Ahmad Al-Qasem, Adan (KW)

(73) Assignee: Kuwait University, Safat (KW)

( * ) Notice: Subject to any disclaimer, the term of this patent is extended or adjusted under 35 U.S.C. 154(b) by 296 days.

(21) Appl. No.: 13/545,710

(22) Filed: Jul. 10, 2012

(65) Prior Publication Data

US 2012/0272753 A1 Nov. 1, 2012

Related U.S. Application Data

(63) Continuation-in-part of application No. 12/662,779, filed on May 3, 2010, now abandoned, which is a continuation-in-part of application No. 11/834,007, filed on Aug. 5, 2007, now abandoned.

(51) Int. Cl.
 - *G01N 1/38* (2006.01)
 - *G01N 35/02* (2006.01)
 - *G01N 35/00* (2006.01)
 - *G01N 1/40* (2006.01)

(52) U.S. Cl.
CPC ........ *G01N 1/38* (2013.01); *G01N 2035/00524* (2013.01); *G01N 2035/00346* (2013.01); *G01N 2035/00534* (2013.01); *G01N 35/025* (2013.01); *G01N 2001/4061* (2013.01)
USPC .................. 73/863.33; 73/863.01; 73/863.11; 73/863.86; 422/64

(58) Field of Classification Search
CPC .................. G01N 1/38; G01N 35/025; G01N 2035/00346; G01N 2035/00524; G01N 2035/00534
USPC ............... 73/863.01, 863.11, 863.33, 863, 86
See application file for complete search history.

(56) References Cited

U.S. PATENT DOCUMENTS

| | | | |
|---|---|---|---|
| 3,437,447 A * | 4/1969 | Harmon | 422/64 |
| 3,525,592 A * | 8/1970 | Buckley | 73/864.12 |
| 3,841,160 A * | 10/1974 | Iwao | 73/864.87 |
| 3,846,075 A * | 11/1974 | Cioffi | 73/863.33 X |
| 4,028,060 A | 6/1977 | Godsey | |
| 4,377,641 A | 3/1983 | Dee et al. | |
| 4,438,205 A | 3/1984 | Saint-Leger et al. | |
| 4,638,674 A | 1/1987 | Redmann | |
| 4,849,110 A | 7/1989 | Takata et al. | |
| 5,013,443 A | 5/1991 | Higashidate et al. | |
| 5,159,818 A | 11/1992 | Etou et al. | |

(Continued)

FOREIGN PATENT DOCUMENTS

| | | | | |
|---|---|---|---|---|
| EP | 0290018 A2 * | 11/1988 | | G01N 35/02 |
| GB | 1218087 A * | 1/1971 | | G01N 1/38 |

(Continued)

*Primary Examiner* — Thomas P Noland
(74) *Attorney, Agent, or Firm* — Richard C Litman

(57) ABSTRACT

The automated sample extraction device is a device for the automatic extraction of chemical samples. The device includes a housing defining an open interior region. A rotating carousel is disposed within the housing, and a plurality of sample holders are mounted thereon. A plurality of sample storage tanks each contain a unique chemical sample, and a desired volume of at least one chemical sample is drawn from a respective one of the sample storage tanks to a respective at least one of the plurality of sample holders. The carousel is rotated so that the desired volume of the at least one chemical sample may be dispensed into a receptacle positioned adjacent the carousel. The at least one chemical sample may then be mixed, heated, cooled, shaken and/or vibrated within the receptacle prior to dispensing.

20 Claims, 9 Drawing Sheets

(56) References Cited

U.S. PATENT DOCUMENTS

| | | | |
|---|---|---|---|
| 5,330,914 | A | 7/1994 | Uhlen et al. |
| 5,576,218 | A | 11/1996 | Zurek et al. |
| 6,197,255 | B1 * | 3/2001 | Miyake et al. ............... 422/64 |
| 6,632,654 | B1 * | 10/2003 | Gebrian et al. ........... 435/287.3 |
| 7,073,403 | B2 | 7/2006 | Albro et al. |
| 7,100,689 | B2 | 9/2006 | Williams et al. |
| 7,105,132 | B2 | 9/2006 | Shumate et al. |
| 7,138,628 | B2 | 11/2006 | Tomimatsu et al. |
| 7,140,264 | B2 | 11/2006 | Zeller |
| 7,152,459 | B2 | 12/2006 | Jen |
| 7,165,444 | B2 | 1/2007 | Zhang et al. |
| 7,389,647 | B1 | 6/2008 | Abraham, III |
| 7,507,337 | B2 | 3/2009 | Petro et al. |
| 2003/0031601 | A1 | 2/2003 | Gebrian et al. |
| 2004/0141880 | A1 | 7/2004 | Handler et al. |
| 2004/0168529 | A1 | 9/2004 | Carlson et al. |
| 2004/0233423 | A1 | 11/2004 | Nakayama et al. |
| 2005/0027088 | A1 | 2/2005 | Nakahara et al. |
| 2005/0153254 | A1 | 7/2005 | Chiu et al. |
| 2006/0054543 | A1 | 3/2006 | Petro et al. |
| 2010/0203573 | A1 | 8/2010 | Heinonen et al. |

FOREIGN PATENT DOCUMENTS

| | | | |
|---|---|---|---|
| JP | 58-196461 | | 11/1983 |
| JP | 60151562 A | * | 8/1985 ............. G01N 35/02 |
| JP | 61082168 A | * | 4/1986 ...................... 422/64 |
| JP | 06241989 A | * | 9/1994 ............. G01N 21/31 |
| JP | 10311837 A | * | 11/1998 ............. G01N 35/02 |
| WO | WO 2009144176 A1 | * | 12/2009 ............... G01N 1/38 |

* cited by examiner

SAMPLE EXTRACTION DEVICE

CROSS-REFERENCE TO RELATED APPLICATION

This application is a continuation-in-part of U.S. patent application Ser. No. 12/662,779, filed on May 3, 2010, which is a continuation-in-part of U.S. patent application Ser. No. 11/834,007, filed on Aug. 5, 2007.

BACKGROUND OF THE INVENTION

1. Field of the Invention

The present invention relates to a devices for the extraction of chemical samples, and particularly to a sample extraction device for automating extraction from one or more chemical samples.

2. Description of the Related Art

Traditional laboratory chemical extraction and manipulation has several drawbacks. Liquid-liquid extraction (LLE) is generally used as a pretreatment process to clean up or pre-concentrate a target species prior to chromatographic analysis of organic substances. Similar techniques are applied in a wide variety of analyses and experiments, such as the study of crude oil mixtures and the like. However, the methods that have traditionally been used in the laboratory for liquid chemical extraction require complicated operation processes, a great deal of time, high cost, particularly when it comes to lost or damaged equipment due to human error, health damage due to the use of organic solvents and the like, and high expense involved with the disposal of toxic organic solvents and the like.

Further, conventional sample extraction and manipulation devices typically only extract and process a single material at a time. Separate devices are often used for related processing steps, such as one device being used for heating and a separate device being used for mixing. In order to increase efficiency, and minimize the possibility of human error, it would be desirable to provide a single system capable of performing multiple processing functions in sample extraction and processing.

Thus, a sample extraction device solving the aforementioned problems is desired.

SUMMARY OF THE INVENTION

The sample extraction device relates to a device for the automatic extraction of chemical samples. One or more chemical samples may be extracted under automatic control, including controlled mixing, heating, cooling, shaking and dispensing thereof. The device includes a housing defining an open interior region. A rotating carousel is disposed within the housing, the carousel having a plurality of sample holders mounted thereon. A plurality of sample storage tanks may each contain a unique chemical sample, and a desired volume of at least one chemical sample may be drawn from a respective one of the plurality of sample storage tanks to a respective at least one of the plurality of sample holders.

The carousel is controllably and selectively rotated so that the desired volume of the at least one chemical sample may be selectively dispensed into a receptacle positioned adjacent the carousel. The at least one chemical sample may then be mixed, heated, cooled, shaken and/or vibrated within the receptacle prior to selective dispensing thereof.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

As will be described in detail below, the sample extraction device 1 allows a user to automatically extract chemical samples. Device 1 is preferably provided as an isolated or unitary integrated system, allowing the user to extract a required quantity of the sample automatically, thus reducing the possibility of human error, in a manner that is relatively quick and has added functionality, such as mixing multiple samples and applying heating, cooling, stirring, shaking and vibration, as will be described in detail below.

Figure 3:
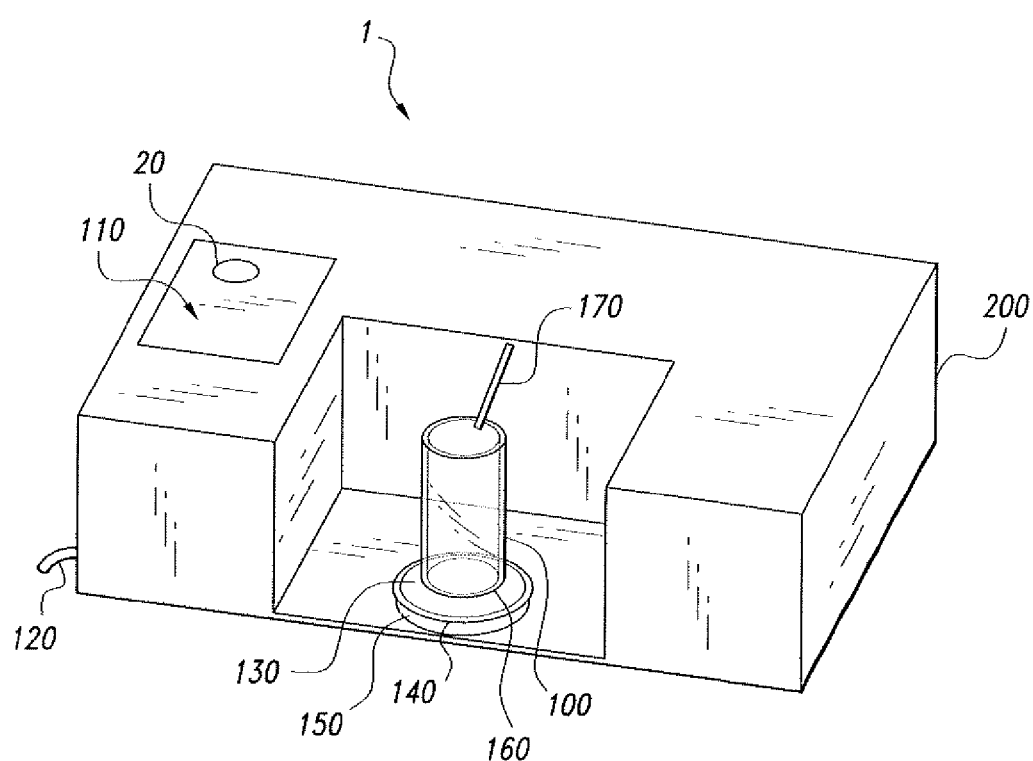
FIG. 3 is a perspective view of the sample extraction device of FIG. 2.
Figure 4:
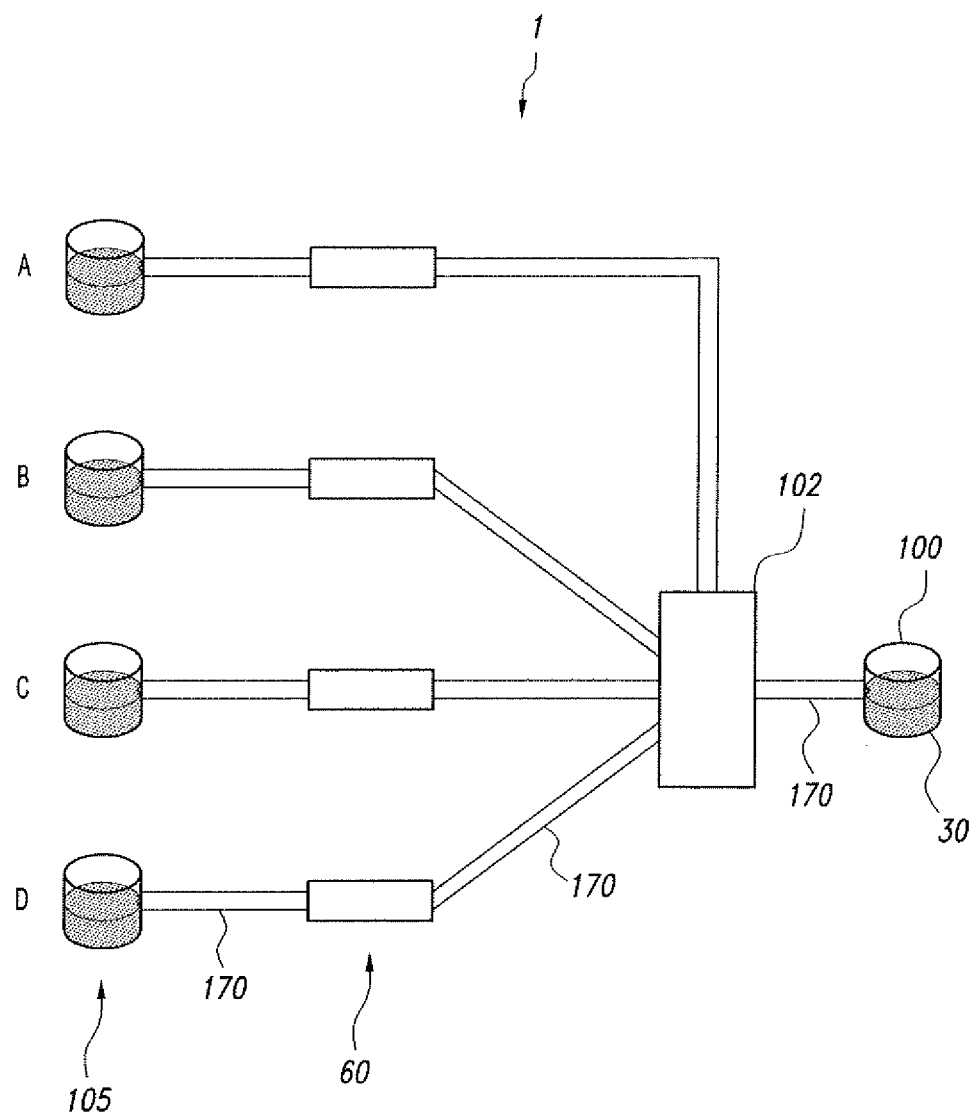
FIG. 4 is a diagrammatic view of a sample extraction device according to the present invention.

The device 1 is operated by a relatively simple user interface (to be described in greater detail below, particularly with regard to the embodiment of FIG. 6 and FIG. 7). In FIG. 3, the device 1 is shown as having a simple button 20, which is pressed to actuate the device and begin the sample extraction. In FIG. 4, the desired sample is shown diagrammatically as 30, contained within an accumulation tank 100. As will be described in greater detail below, particularly with regard to the embodiment of FIG. 6 and FIG. 7, a controller 202 is provided. The user inputs the chemical properties of the desired sample into the controller 202 (via any suitable interface, as will be described below), along with the desired quantity of the sample, and then presses the operation button 20 to extract the sample, which is collected in the accumulation tank 100. If more than one sample is desired (i.e., multiple samples are extracted to produce a mixed end result), the additional samples are extracted at the same time and also placed within the accumulation tank 100. As will be described in greater detail below, the device 1, under the control of the controller 202, automatically mixes, heats, cools, stirs and/or shakes the sample contained within the tank 100, depending upon the desired end product.

FIG. 4 diagrammatically illustrates the device 1, shown having a set of tanks 105, including four tanks, namely tank A, tank B, tank C and tank D. It should be understood that any suitable number of tanks may be provided. In the embodiment of FIG. 6, as will be described in greater detail below, a far greater number of different sample materials may be used.

The four tanks A, B, C and D of set 105 each contain a unique chemical sample. Each tank of set 105 is connected to a pump 60, which may be any suitable type of pump under control of the controller 202, via a respective conduit 170. The desired samples, in desired volumes, are drawn by conduits 170 (under pressure generated by pumps 60) into a central mixing chamber 102, and then dispensed into the accumulation tank 100 as the final product 30.

Figure 1:
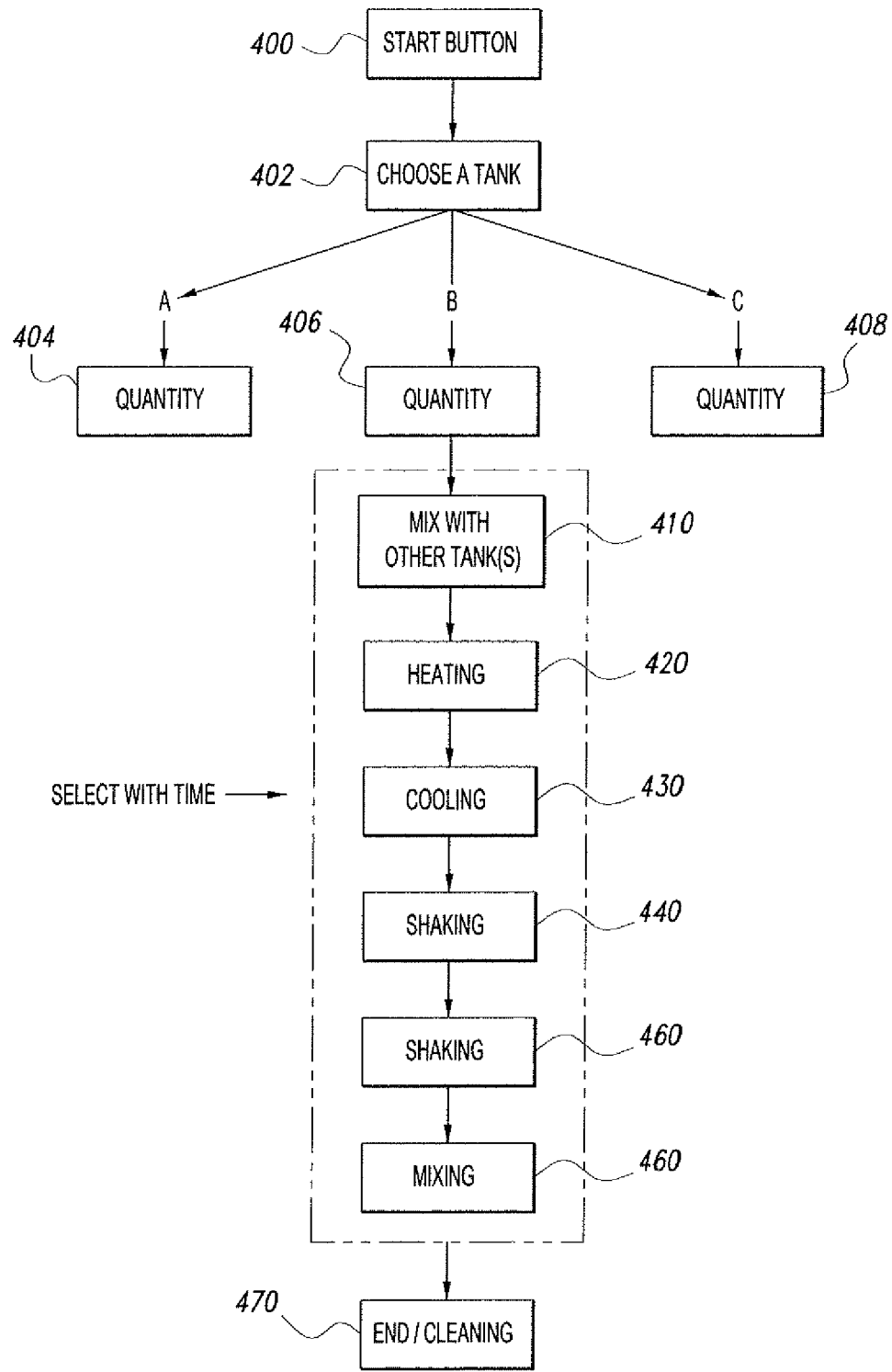
FIG. 1 is a flowchart illustrating a method of using a sample extraction device according to the present invention.

As shown in FIG. 1, the user begins operation by pressing button 20 at step 400. The user may then either manually choose one or more of tanks A, B, C and D of set 105, or the controller 202 automatically determines which samples are required, and in which quantities, depending upon the user's initial input of the desired end product. This choice is made at step 402. In the particular example of FIG. 1, only the samples in tanks A, B and C are required to produce the desired end product 30.

The particular quantities of each are drawn off at 404, 406 and 408, respectively, and delivered into the mixing chamber 102 (of FIG. 4). Mixing occurs at step 410, and any required subsequent heating, cooling, shaking or additional mixing (or stirring) occurs at steps 410, 420, 430, 440, 460, respectively. The user may initiate heating, cooling, shaking or additional mixing (or stirring) manually, or the controller 202 may initiate these steps automatically, with particular instructions for the production of varying substances being stored within computer readable memory 302.

Figure 5:
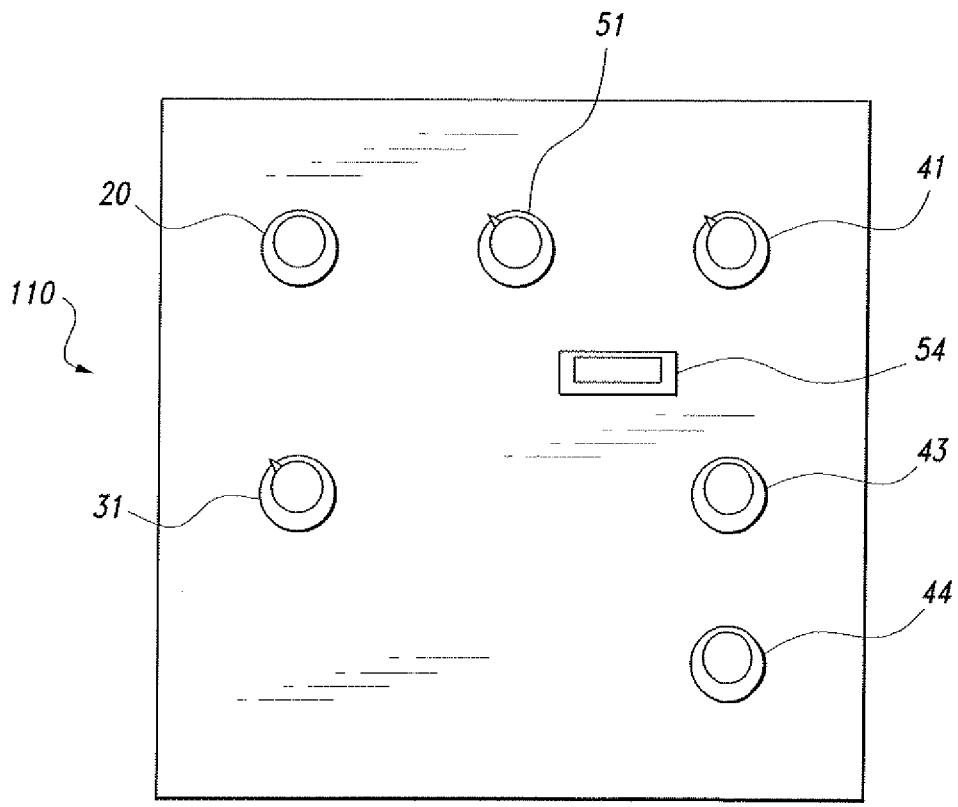
FIG. 5 is a plan view of a control panel for the sample extraction device of FIG. 3.

FIG. 5 illustrates a control panel interface 110 and, after completion of the preparation of sample 30, the user may press a completion button 43, thus allowing the user to remove the completed sample and also beginning an automated internal cleaning process of the conduits, etc. of device 1 (step 470). The cleaning process of device 1 may be actuated at any time, not just after production of sample 30, by depressing a cleaning button 44 of control panel 110.

Figure 2:
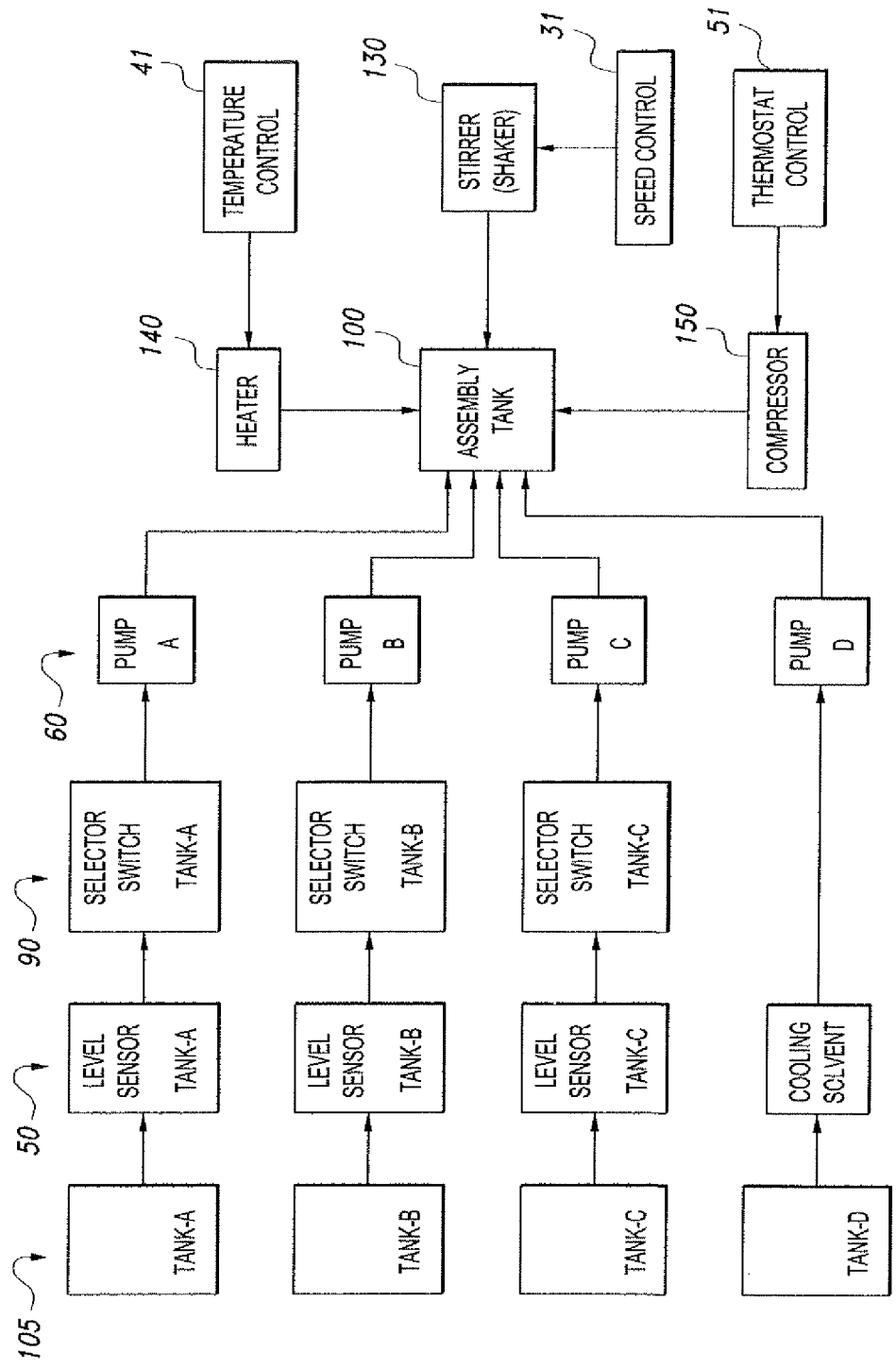
FIG. 2 is a block diagram illustrating the system components of a sample extraction device according to the present invention.

As shown in FIGS. 2 and 3, the device 1 includes the set of tanks 105, a heater 140, the accumulating tank 100, a liquid level sensor and controller 50, a plurality of pumps 60, a temperature controller 41 for the heater 140, a stirrer controller 31, a stirrer 130, a cooler 150, such as a compressor cooling system or the like, a temperature controller or thermostat 51 for the cooler 150, and a set of selector switches 90. Any suitable type of heater 140 may be used to heat the contents of the assembly tank 100. Similarly, any suitable type of cooler 150 may be used to chill the contents of the assembly tank 100, and any suitable type of stirrer, mixer or vibrator 130 may be used to stir, mix, vibrate or shake the contents of assembly tank 100. The user may manually actuate each through respective controllers 41, 51, 31, or the controllers 41, 51, 31 may be pre-programmed automatic controllers. Alternatively, as will be described in greater detail below, the controllers 41, 51, 31 may be in communication with the controller 202, or may be integrated as components thereof.

In FIG. 3, the device 1 is shown as having a housing 200 to which the control panel 110 is mounted (FIG. 5 illustrates a plan view of the control panel 110). Preferably, the housing 200 has a drain 120 to drain any liquids collected within the housing 200. The assembly tank 100 sits in front of the housing 200, the housing 200 extending around the sides of the assembly tank 100. The assembly tank 100 sits on an assembly tank holder 130, which contains the heater 140, the cooler 150 and the stirrer 160. Additionally, the conduits 170 leading from the set of tanks 105 are further shown in FIG. 3, positioned above an open end of the assembly tank 100.

Additionally, as illustrated in FIG. 2, a liquid level sensor and liquid level control switch 50 is associated with each tank of the set of tanks 105. Each liquid level sensor 50 is in communication with the controller 202 and with the pumps 60 for measuring the volume of liquid drawn out of each tank. Once a desired volume has been drawn off, the control switch deactivates the respective pump. Additionally, separate selector switches 90 may be applied to one or more of the tanks of set 105, allowing for either manual or automatic (under control of controller 202) actuation of the pumps 60. In the example of FIG. 2, three separate samples are provided in tanks A, B and C, and tank D is provided for containing water and/or a cooling solvent for the cleaning process described above.

In the control panel 110 of FIG. 5, the temperature controller 41 for heater 140 is shown as a manual switch. The temperature controller may be a manual on/off type switch, and may be a dial or the like allowing for input of a desired temperature, or may be controlled by the controller 202 or otherwise automatically, as described above. An indicator lamp 54 is provided to indicate to the user that the desired temperature has been reached. Similarly, the temperature controller 51 for the heater 150 is shown as a manual switch. The temperature controller 51 may be a manual on/off type switch, may be a dial or the like allowing for input of a desired temperature, or may be controlled by the controller 202 or otherwise automatically, as described above. The indicator lamp 54 indicates to the user that the desired temperature has been reached. The stirrer control switch 31 is similarly mounted on control panel 110.

When the device 1 is actuated, the samples from the three primary tanks A, B and C of set 105 flow to the accumulating tank 100 and are heated or cooled to the pre-set desired temperature, along with any necessary stirring, set to a desired time. The accumulating tank 100 may be removed from housing 200 and the produced sample can be stored in the accumulating tank 100 or another vessel.

When the process is finished, the user presses the cleaning button 44, at which point the water from tank D will flow through the path in which the samples passed, thus cleaning the unit. The user then disposes of the water from the accumulating tank 100.

As an example, if a user is conducting an experiment to measure the salt in a crude oil sample, the user may require three samples to perform the experiment, namely crude oil, mixed alcohol and saline. Tanks A, B and C are filled with crude oil, mixed alcohol and saline solution, respectively. The user may then input a desired quantity of crude oil, such as 10 cubic centimeters to be extracted. Level sensor 50 controls operation of the pump 60 to fill the assembly tank 100. The desired quantity may be manually input by the user, or the quantities, properties and instructions for preparation of particular experiments or end result substances may be stored in a database contained in memory 302 of the controller 202.

Similarly, 40 cubic centimeters, for example, of the mixed alcohol may be drawn off, as well as a desired quantity of saline, to be mixed together in assembly tank 100. The three separate substances, which were drawn simultaneously and dispensed into the assembly tank 100, may then be mixed together, either by manual actuation of the mixer or under automatic control of the controller 202, following the instructions stored in the database in the memory 302 for this particular experiment and substance. Similarly, heating and cooling may be manually controlled or automatically controlled by controller 202.

Figure 6:
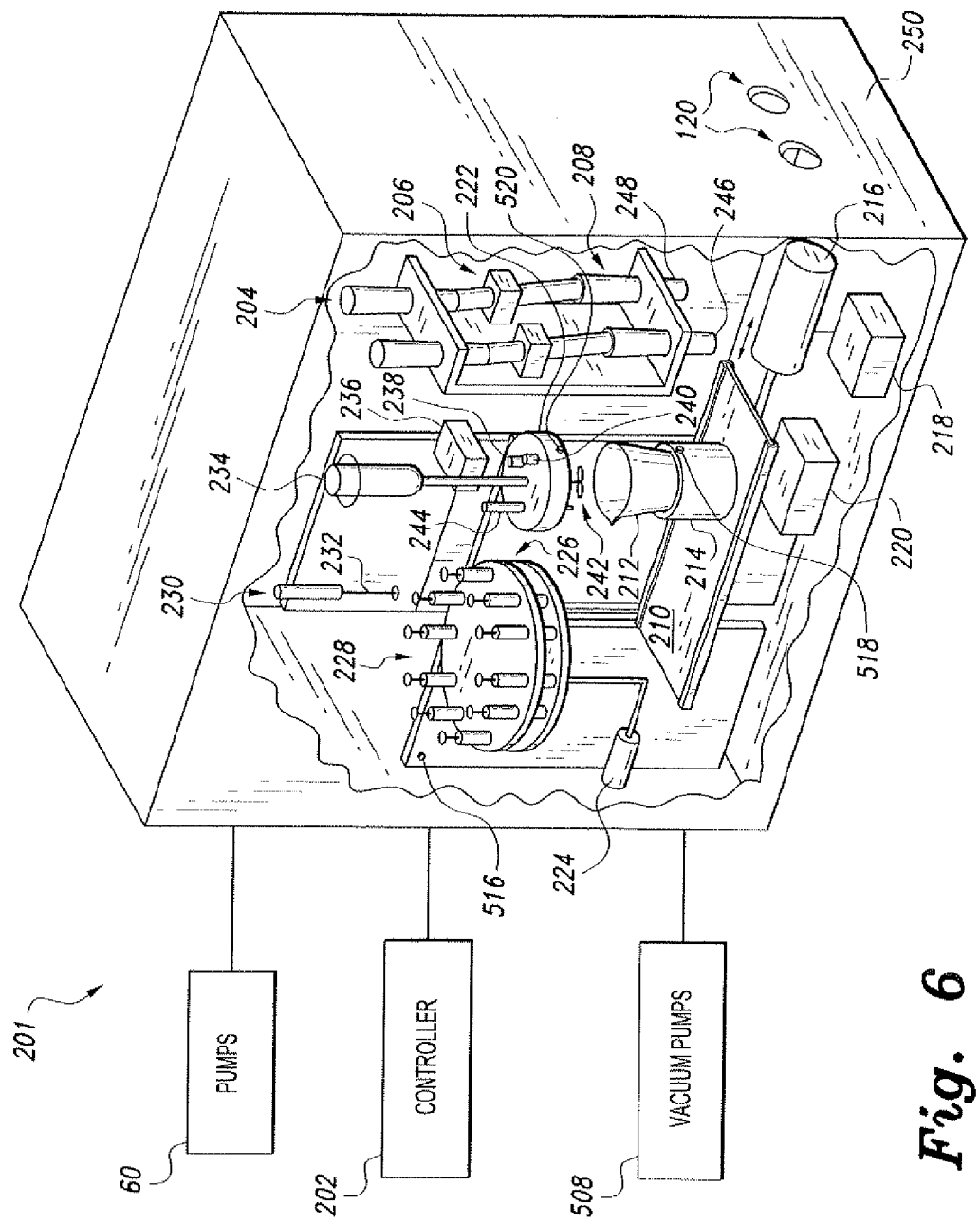
FIG. 6 is a perspective view of an alternative embodiment of a sample extraction device according to the present invention, the housing being broken away to show the arrangement of components therein.

In the alternative embodiment of FIG. 6, the system 201 allows for the controlled extraction and manipulation of a plurality of samples. As in the previous embodiment, pumps 60 feed the substances contained within storage tanks 105, under the control of controller 202, to a plurality of sample holders 228 contained within housing 250. As shown in FIG. 6, any desired number of sample holders 228 may be utilized, allowing for the extraction of more than four different substances (such as those contained in tanks A, B, C and D of the previous embodiment).

Figure 8:
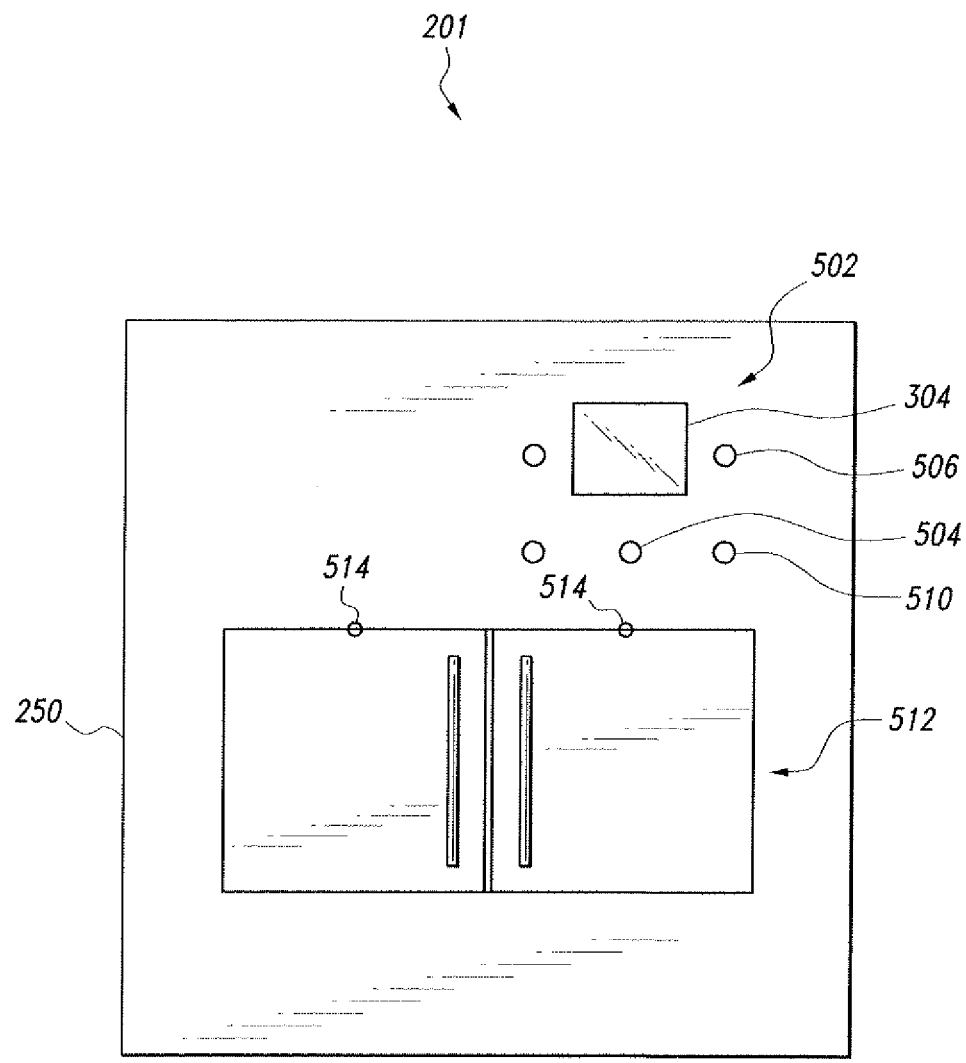
FIG. 8 is a side view of the sample extraction device of FIG. 6.

FIG. 8 illustrates an alternative control panel 502 mounted on the side of the housing 250 of the system 201. Initiation of the process begins through actuation of a button or switch 504. An indicator light 506 indicates that processing has begun. A display 304 is provided for displaying data to the user and may further be a touchscreen or the like, further providing the user with input capability. Upon initiation of the system 201, one or more vacuum pumps 508 are actuated for removal of ambient air from within the housing 250. Preferably, the air from within housing 250 is drawn to standard laboratory ventilation, including appropriate filtering, before passage to the exterior environment. The actuation of the vacuum pumps 508 may be initiated manually by a key 510, a switch, or the like on the control panel 502.

The vacuum pump process preferably only begins after the closing and sealing of doors 512, which are mounted in the side of the housing 250, as shown in FIG. 8. Preferably, the doors 512 are monitored by sensors 514, which may be any conventional type of sensors, microswitches or the like, which detect whether or not the doors 512 are closed and sealed. If the doors 512 are open and the user attempts to initiate the first processing step (i.e., actuation of the vacuum pumps 508), an alert message is delivered to the user on the display 304. Further, the sensors 514 are in communication with the controller 202, and if the doors 512 are opened during any part of sample extraction or chemical processing, the system 201 will be shut down to prevent accidental contamination of the laboratory or injury to a user.

The samples 228, which may be blood samples, crude petroleum, or any other substance to examined and processed, are preferably placed manually into slots or holders of a carousel 226, as shown, through the access doors 512. Rotation of the carousel 226 for manual placement of samples 228 may be accomplished through user commands entered through the control panel 502 and monitored on the display 304. The user may also enter logging information regarding each sample 228. Angular positioning of the carousel 226 may be monitored by a sensor 516, microswitch or the like.

Any suitable rotatable drive may be used to provide selective and controlled rotation of the carousel 226, which is mounted within the housing 250, as shown. In FIG. 6, a hydraulic or pneumatic cylinder 224, under the control of the controller 202, drives rotation of the carousel 226, although it should be understood that this is shown for exemplary purposes only, and that any suitable type of drive system may be utilized.

A beaker 212 (replacing assembly tank 100) is mounted on a sliding platform 210, as shown. Preferably, the beaker 212 is mounted on a temperature control unit 214, which may be a Peltier heater/cooler or the like, which rests on platform 210. The temperature control unit 214 is in communication with the controller 202 for controlled actuation for the selective heating or cooling of the contents of the beaker 212. The sliding platform 210 may be translated by a pneumatic cylinder 216 or the like, in communication with a motor 218, or by any other suitable type of linear actuator under the control of the controller 202. Preferably, a sensor 518, microswitch or the like is provided in unit 214 for monitoring proper placement of the beaker 212. An alert may be sent to the user on the display 304 if the beaker is not in place or is off-balance. The displacement or breaking of the beaker 212 may be monitored by sensor 518 throughout the entire processing process, and the system 201 can be automatically shut down in such an event. The particular processing to be performed, as shown in the flowchart of FIG. 1, may be programmed by the user into the controller 202 through the touchscreen display 304 or the like.

Once the contents of the tanks 105 have been pumped into the respective sample holders 228, the platform 210 is slid underneath the carousel 226. The carousel 226 is then rotated so that a desired one of the sample holders 228 is positioned beneath plunger 232 of piston 230 (and over the open upper end of the beaker 212). The piston 230 may be hydraulic, pneumatic or any other type of linear actuator driven by motor or fluid source 236, under the control of the controller 202, to selectively drive the plunger 232 into the selected sample holder 228 to dispense a desired volume of the sample into the beaker 212.

Desired volumes of one or more different substances from sample holders 228 may be dispensed into the beaker 212. Following dispensing, the platform 210 is then slid back to the position illustrated in FIG. 6, beneath a cover 222. A piston 234, which may also be in communication with motor or fluid source 236, lowers the cover 222 onto the beaker 212 to seal the upper end thereof. The piston 234 may be a hydraulic piston, a pneumatic piston, a linear actuator or the like, under the control of the controller 202. As shown, a thermocouple 244, in communication with the controller 202, is mounted to the cover 222 to at least partially project into the contents of the beaker 212. The thermocouple 244 is used to measure the temperature of the beaker 212, and the temperature control unit 214 may be actuated to selectively heat or cool the beaker to a desired temperature. Preferably, the cover 222 has a sensor 520, microswitch, or the like for monitoring the closure and sealing of the cover 222 on the beaker 212. If the seal is broken during processing, or if the cover 222 fails to properly cover the beaker 212, the system 201 can be shut down so that the sample within the beaker 212 does not accidentally spill and/or contaminate the system or environment. An alert can also be delivered to the user on the display 304. The temperature and time of heating or cooling may be monitored and/or controlled by the user via the control panel 502.

Additionally, motor 220, also under the control of the controller 202, may be actuated to shake the platform 210, thus shaking the contents of beaker 212. Any suitable type of shaker or vibrator may be utilized. The amplitude and frequency of vibration is controlled by the controller 202. In addition to the shaking, a mixer 242 is rotatably mounted to the cover 222, as shown, the mixer 242 being powered by motor 236 to selectively and controllably mix the contents of the beaker 212 for a controlled duration and at a controlled rotational velocity. Shaking and mixing may be also be monitored and controlled (intensity and time) by the user via the control panel 502.

Following shaking, mixing and temperature adjustment to desired pre-set parameters (via the controller 202), the platform 210 is slid to the right (in the orientation of FIG. 6) so that ports 238, 240 formed through the cover 222 align with the lower ends 248, 246, respectively, of dispenser tubes 204. External pumps or the like may then be actuated to draw off the contents of the beaker 212 to an external dispenser. Valves 206 may be mounted within the dispenser 204, as shown, for selective and controlled flow. Valves 206 may be controllable air valves or the like. Alternatively, the beaker 212 may simply be removed from within the housing 250, as in the previous embodiment, allowing the end result to be stored and transported therein.

Figure 9:
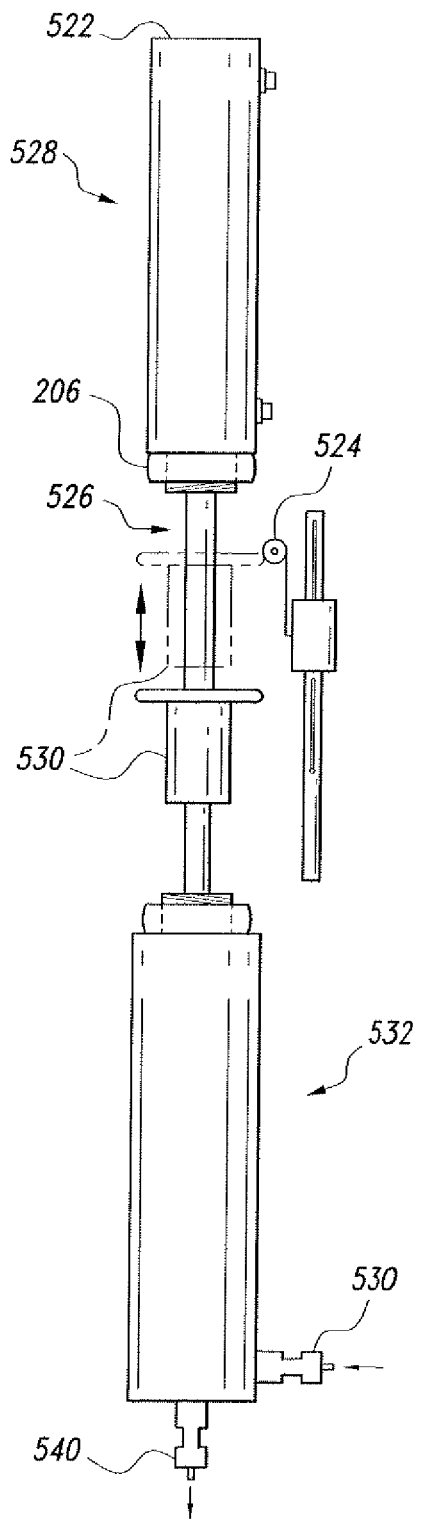
FIG. 9 is a side view of an alternative embodiment of the dispenser tube of the sample extraction device of FIG. 6.

FIG. 9 illustrates an alternative embodiment of a dispenser tube 528, similar to the dispenser tube 204 of FIG. 6. The dispenser tube 528 includes an air cylinder 522, pump or the like for drawing on a sliding portion 530, which is slidably mounted on a shaft 526. When a negative pressure is established, the sliding portion 530 is drawn upward until contact between an upper end 523 with a stop 524 is made. Stop 524 may be vertically adjusted to a desired height, thus controlling an amount of fluid to be drawn from the beaker 212.

In operation, when the beaker 212 and the cover 222 are moved beneath the dispenser tubes 528, the beaker 212 and the cover 222 are positioned directly beneath a lower container 532. As shown in FIG. 9, preferably input and output one-way valved ports 530, 540 are formed on the lower end of container 532, for drawing the fluid into container 532 and outputting the fluid to external storage. The sliding portion 530 is linked to a piston or the like within the container 532, and upward motion of the sliding portion 530, drawn by pump 522, draws fluid from the beaker 212 into the container 532, similar in action to a syringe. The vertical positioning of stop 524 controls how far the sliding portion 530 travels, thus controlling the volume of fluid drawn into the container 532.

Figure 7:
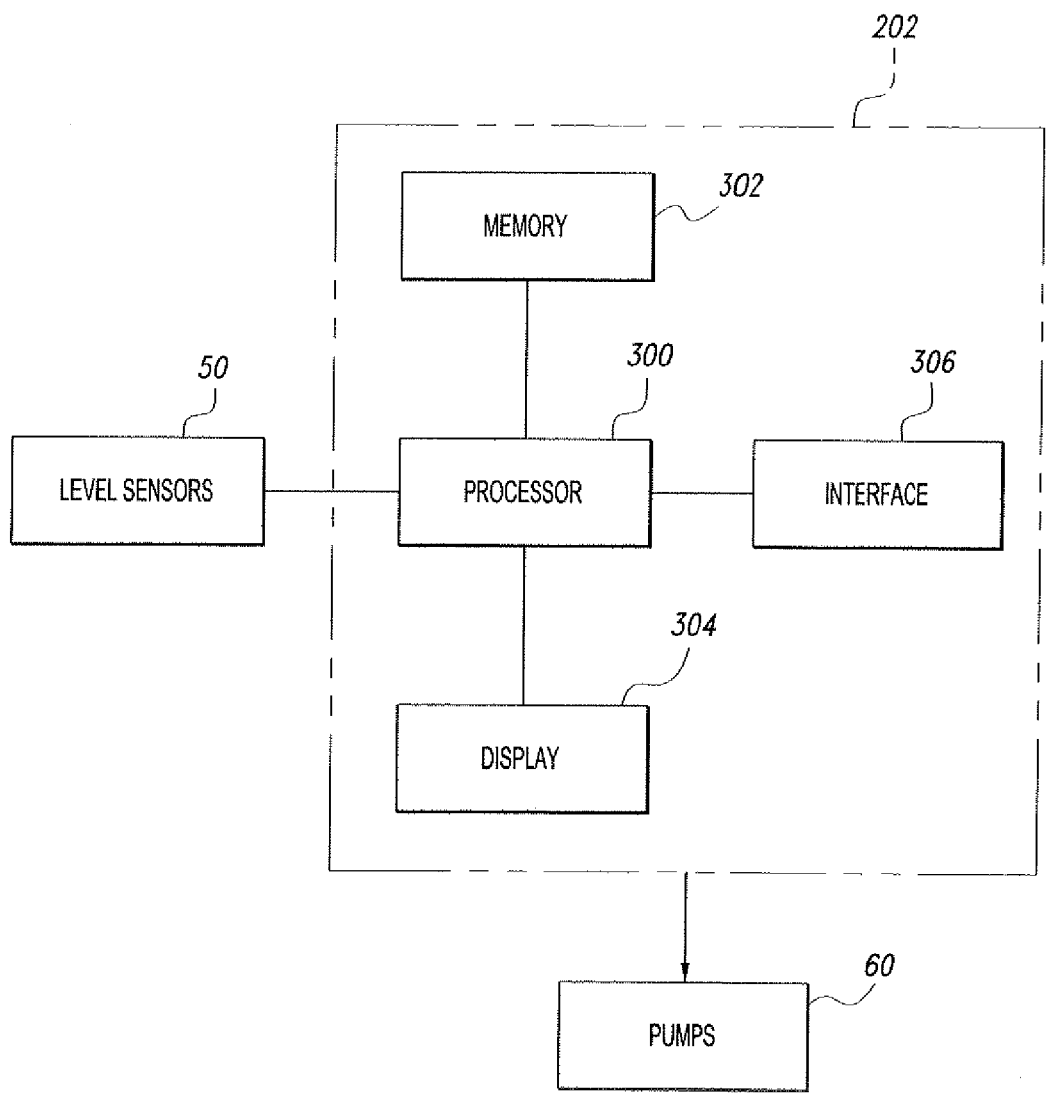
FIG. 7 is a block diagram illustrating components of a controller of a sample extraction device according to the present invention.

FIG. 7 illustrates the controller 202, which includes a processor 300 in communication with the display 304, computer readable memory 302 and an interface 306. Data is entered into processor 300 via any suitable type of user interface 306, and may be stored in memory 302, which may be any suitable type of computer readable and programmable memory. Calculations are performed by the processor 300, which may be any suitable type of computer processor and may be displayed to the user on the display 304, which may be any suitable type of computer display.

The processor 300 may be associated with, or incorporated into, any suitable type of computing device, for example, a personal computer or a programmable logic controller. The display 304, the processor 300, the memory 302 and any associated non-transitory computer readable recording media are in communication with one another by any suitable type of data bus, as is well known in the art.

Examples of computer readable recording media include a magnetic recording apparatus, an optical disk, a magneto-optical disk, and/or a semiconductor memory (for example, RAM, ROM, etc.). Examples of magnetic recording apparatus that may be used in addition to memory 302, or in place of memory 302, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

It should be understood that any type of processing steps and/or monitoring properties may be programmed into the controller, as desired by the user and as required by a particular sample process. Additional monitors, sensors, microswitches and the like may also be used, dependent upon the particular desires of the user.

It is to be understood that the present invention is not limited to the embodiment described above, but encompasses any and all embodiments within the scope of the following claims.

I claim:

1. An automated sample extraction device, comprising:
a housing defining an open interior region;
a rotating carousel disposed within the housing, the rotating carousel having a plurality of sample holders mounted thereon;
a plurality of sample storage tanks adapted for containing a unique chemical sample;
means for drawing a desired volume of at least one of the chemical samples from a respective one of the plurality of sample storage tanks to a respective at least one of the plurality of sample holders;
means for selectively rotating the rotating carousel so that the desired volume of the at least one chemical sample may be selectively dispensed into a receptacle positioned adjacent the carousel;
a cover selectively sealing an open upper end of the receptacle;
means for selectively mixing the at least one chemical sample contained within the receptacle; and
means for dispensing the at least one chemical sample from the receptacle.

2. The automated sample extraction device as recited in claim 1, wherein said receptacle is selectively positioned beneath said carousel.

3. The automated sample extraction device as recited in claim 2, further comprising means for selectively heating the at least one chemical sample contained within the receptacle.

4. The automated sample extraction device as recited in claim 3, further comprising means for selectively cooling the at least one chemical sample contained within the receptacle.

5. The automated sample extraction device as recited in claim 4, further comprising means for measuring the temperature of the at least one chemical sample contained within the receptacle, the means for measuring the temperature being in communication with said means for selectively heating and said means for selectively cooling the at least one chemical sample for selective actuation and deactuation thereof.

6. The automated sample extraction device as recited in claim 5, further comprising means for selectively covering and uncovering said receptacle with the cover.

7. The automated sample extraction device as recited in claim 6, wherein said means for selectively mixing the at least one chemical sample and said means for measuring the temperature of the at least one chemical sample are mounted to the cover.

8. The automated sample extraction device as recited in claim 7, further comprising means for selectively moving said receptacle from beneath said carousel to a position beneath the cover.

9. The automated sample extraction device as recited in claim 8, wherein said means for selectively moving said receptacle from beneath said carousel to the position beneath the cover comprises a sliding platform, said receptacle and said means for heating and said means for cooling the at least one chemical sample being mounted on the sliding platform.

10. The automated sample extraction device as recited in claim 9, further comprising means for vibrating the sliding platform.

11. The automated sample extraction device as recited in claim 1, wherein said housing has a drain formed therethrough.

12. The automated sample extraction device as recited in claim 1, wherein one of said sample storage tanks has a cleaning fluid contained therein.

13. The automated sample extraction device as recited in claim 1, further comprising means for monitoring whether said cover is sealed to said receptacle.

14. An automated sample extraction device, comprising:
a housing defining an open interior region;
a rotating carousel disposed within the housing, the rotating carousel having a plurality of sample holders mounted thereon;

a plurality of sample storage tanks, each of the tanks being adapted for containing a unique chemical sample;

means for drawing a desired volume of at least one of the chemical samples from a respective one of the plurality of sample storage tanks and transferring the drawn volume to a selected one of the sample holders;

means for selectively rotating the rotating carousel so that the desired volume of the at least one chemical sample may be selectively dispensed into a receptacle positioned adjacent the carousel;

a cover selectively sealing an open upper end of the receptacle;

means for selectively heating the at least one chemical sample is contained within the receptacle;

means for selectively mixing the at least one chemical sample contained within the receptacle; and means for dispensing the at least one chemical sample from the receptacle.

15. The automated sample extraction device as recited in claim 14, wherein said receptacle is selectively positioned beneath said carousel.

16. The automated sample extraction device as recited in claim 15, further comprising means for selectively cooling the at least one chemical sample contained within the receptacle.

17. The automated sample extraction device as recited in claim 16, further comprising means for measuring the temperature of the at least one chemical sample contained within the receptacle, the means for measuring the temperature being in communication with said means for selectively heating and said means for selectively cooling the at least one chemical sample for selective actuation and deactuation thereof.

18. The automated sample extraction device as recited in claim 17, further comprising means for selectively covering and uncovering said receptacle with the cover.

19. The automated sample extraction device as recited in claim 18, wherein said means for selectively mixing the at least one chemical sample and said means for measuring the temperature of the at least one chemical sample are mounted to the cover.

20. The automated sample extraction device as recited in claim 14, further comprising means for monitoring whether said cover is sealed to said receptacle.

* * * * *